(12) United States Patent
Shinya et al.

(10) Patent No.: US 8,053,194 B2
(45) Date of Patent: Nov. 8, 2011

(54) LABELING SUBSTANCE AND CHIMERIC SUBSTANCE AND METHOD FOR PREPARING THE SAME AND METHOD FOR CAPTURING, STRUCTURALLY ANALYZING AND/OR IDENTIFYING BIOLOGICAL SUBSTANCE BY MEANS OF THE LABELING SUBSTANCE

(76) Inventors: Kazuo Shinya, Tokyo (JP); Tohru Natsume, Tokyo (JP); Takayuki Doi, Yokohama (JP)

(*) Notice: Subject to any disclaimer, the term of this patent is extended or adjusted under 35 U.S.C. 154(b) by 1073 days.

(21) Appl. No.: 10/594,119

(22) PCT Filed: Mar. 30, 2005

(86) PCT No.: PCT/JP2005/006077
§ 371 (c)(1),
(2), (4) Date: May 31, 2007

(87) PCT Pub. No.: WO2005/094187
PCT Pub. Date: Oct. 13, 2005

(65) Prior Publication Data
US 2007/0287152 A1  Dec. 13, 2007

(30) Foreign Application Priority Data

Mar. 31, 2004 (JP) ................. 2004-102879
Apr. 6, 2004 (JP) ................. 2004-112335

(51) Int. Cl.
*G01N 33/00* (2006.01)
*G01N 33/53* (2006.01)
*G01N 33/566* (2006.01)
*C07K 5/00* (2006.01)

(52) U.S. Cl. ............ 435/7.1; 435/7.92; 436/56; 436/63; 436/501; 436/513; 530/328

(58) Field of Classification Search .................. None
See application file for complete search history.

(56) References Cited

U.S. PATENT DOCUMENTS
6,197,527 B1   3/2001   Lynch et al.
(Continued)

FOREIGN PATENT DOCUMENTS
EP     0 488 152 A2   6/1992
(Continued)

OTHER PUBLICATIONS

Yu et al., "A high-throughput assay for assessing the cell permeability of combinatorial libraries," Nature Biotechnology, 2005, vol. 23, No. 6, pp. 746-751.*

(Continued)

*Primary Examiner* — Shafiqul Haq
*Assistant Examiner* — Galina Yakovleva
(74) *Attorney, Agent, or Firm* — Roberts Mlotkowski Safran & Cole P.C.

(57) ABSTRACT

Disclosed is a labeling substance capable of reversibly immobilizing (reversible detachment) to a solid surface and to reliably and accurately identify a target biological substance interacting with a probe substance bound to the labeling substance. A chimeric compound is provided, which includes a labeling substance L including (1) an organic compound S with a chemical structure capable of binding to a probe substance P, which can interact with a biological substance B and (2) a peptide bound to the organic compound S and specifically recognized by an antibody A, peptide and a probe substance P at least except a peptide or protein. In addition, a method for preparing the labeling substance L and a method for capturing, structurally analyzing and/or identifying the biological substance using the labeling substance L are provided.

8 Claims, 15 Drawing Sheets

U.S. PATENT DOCUMENTS

| | | | |
|---|---|---|---|
| 2002/0068367 A1 | 6/2002 | Coffen et al. | |
| 2002/0182597 A1 | 12/2002 | Kuimelis et al. | |
| 2004/0038319 A1 | 2/2004 | Aebersold et al. | |
| 2006/0234229 A1* | 10/2006 | Van Beuningen et al. | 435/6 |

FOREIGN PATENT DOCUMENTS

| | | | |
|---|---|---|---|
| WO | WO-95/16209 A1 | | 6/1995 |
| WO | 00/11208 A1 | | 3/2000 |
| WO | WO 0011208 A1 | * | 3/2000 |
| WO | 02/33044 A2 | | 4/2002 |
| WO | 02055547 A2 | | 7/2002 |

OTHER PUBLICATIONS

European Office Action dated Sep. 17, 2008 issued in corresponding European Patent Application No. 05 721 660.8.

Mitsuaki Yanagida et al., "Isolation and Proteomic Characterization of the Major Proteins of the Nucleolin-binding Ribonucleoprotein Complexes," *Proteomics* 2001, 1, pp. 1390-1404.

Einhauer, A.; Jungbauer, A.; "The Flag peptide, a versatile fusion tag for the purification of recombinant proteins", Journal of Biochemical and Biophysical Methods, vol. 49, 2001, pp. 455-465.

Kiick, Kristi L.; Saxon, Eliana; Tirrell, David A.; and Bertozzi, Carolyn R.; "Incorporation of azides into recombinant proteins for chemoselective modification by the Staudinger ligation", Proceedings of the National Academy of Sciences of the United States of America, Jan. 8, 2002, vol. 99, No. 1, pp. 19-24.

Jans, David A.; Bergmann, Lothar; Peters, Reiner; and Fahrenholz, Falk; "Biotinyl Analogues of Vasopressin as Biologically Active Probes for Vasopressin Receptor Expression in Cultured Cells", The Journal of Biological Chemistry, vol. 265, No. 24, Aug. 25, 1990, pp. 14599-14605.

European Office Action dated Mar. 18, 2009 issued in corresponding European Patent Application No. 05 721 660.8.

Office Action issued on Dec. 21, 2010 in corresponding JP Application No. 2006-511728 and partial English translation of the Notice of Reasons for Refusal.

* cited by examiner

[Fig. 1]
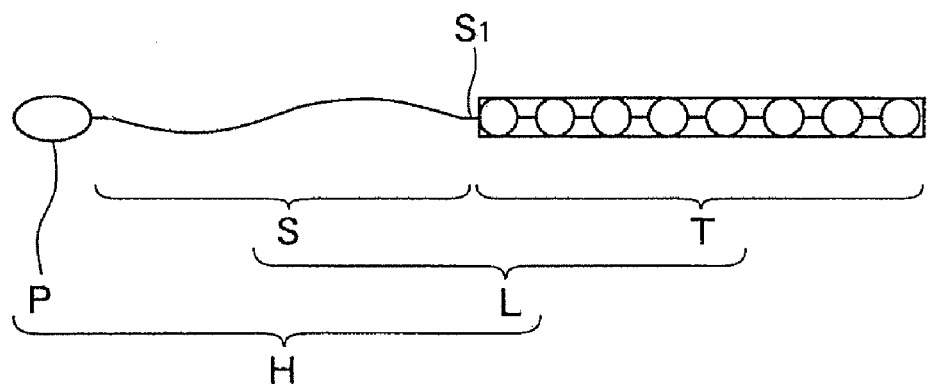

[Fig. 2]
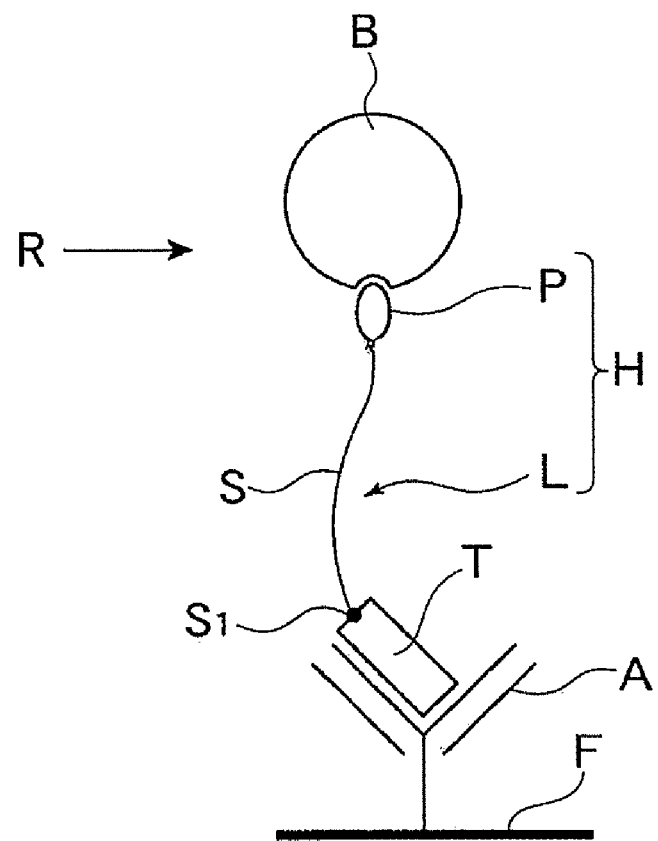

[Fig. 3]
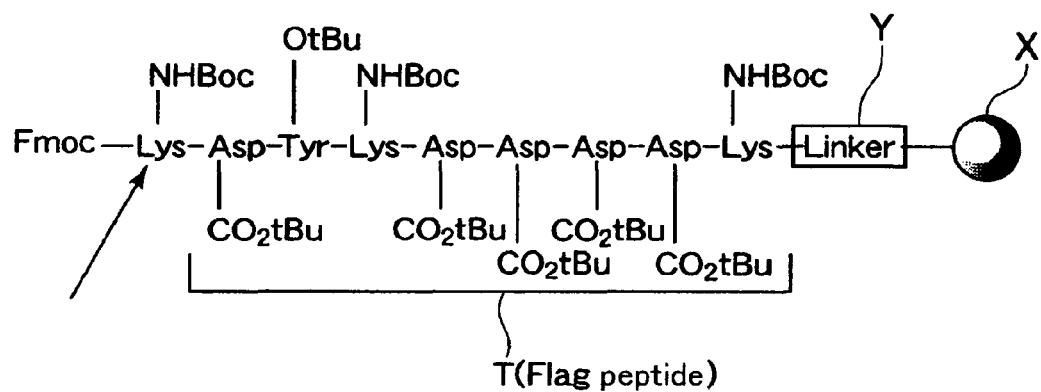

[Fig. 4]
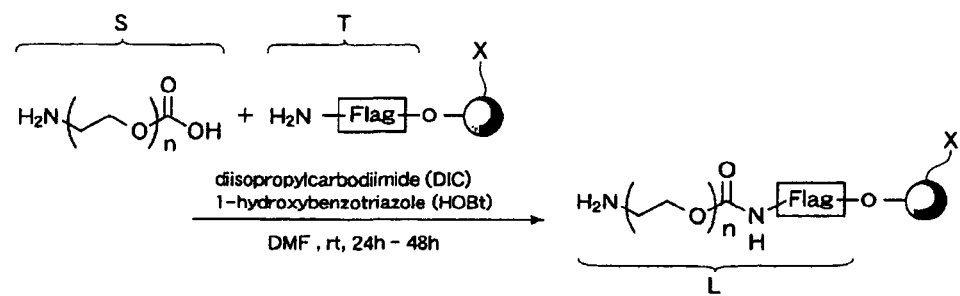

[Fig. 5]
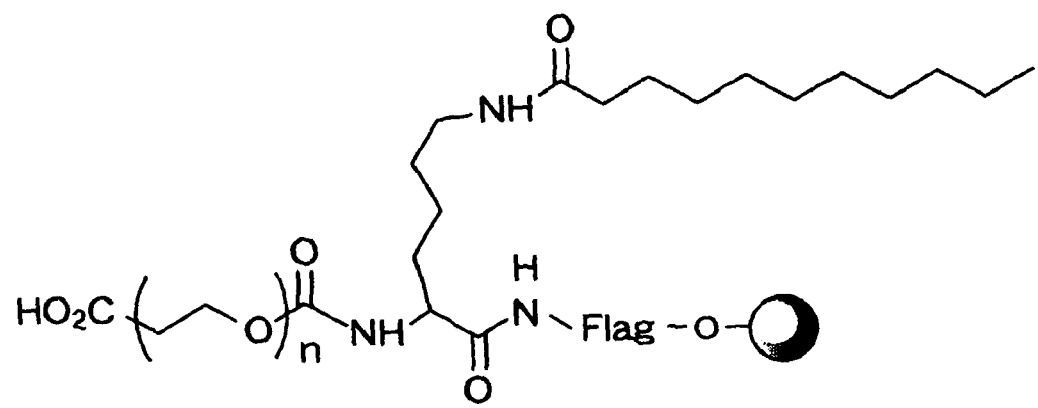

[Fig. 6]
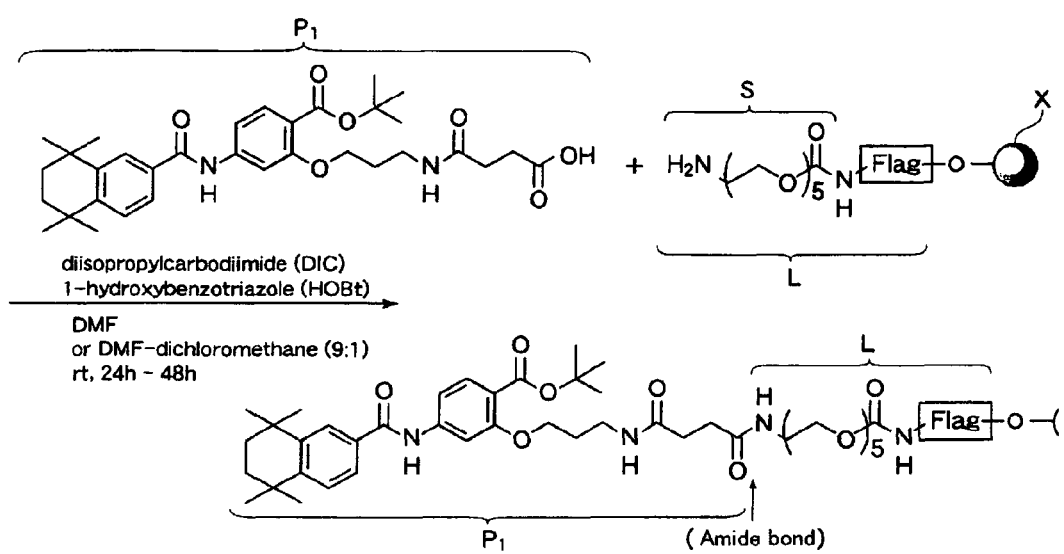

[Fig. 7]
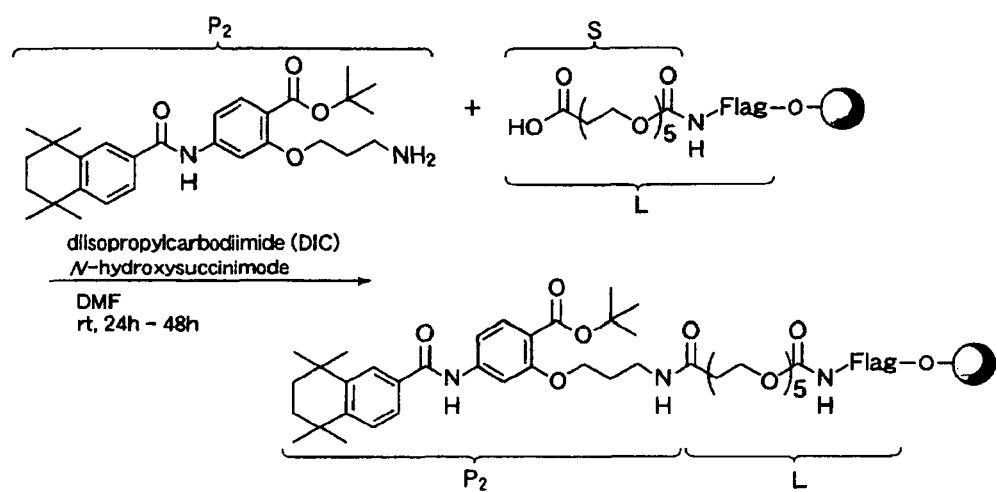

[Fig. 8]
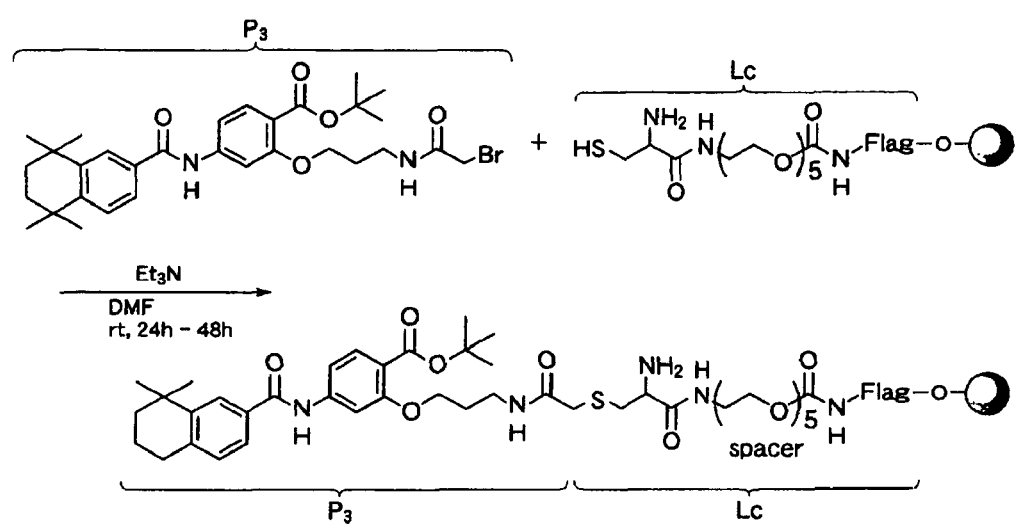

[Fig. 9]
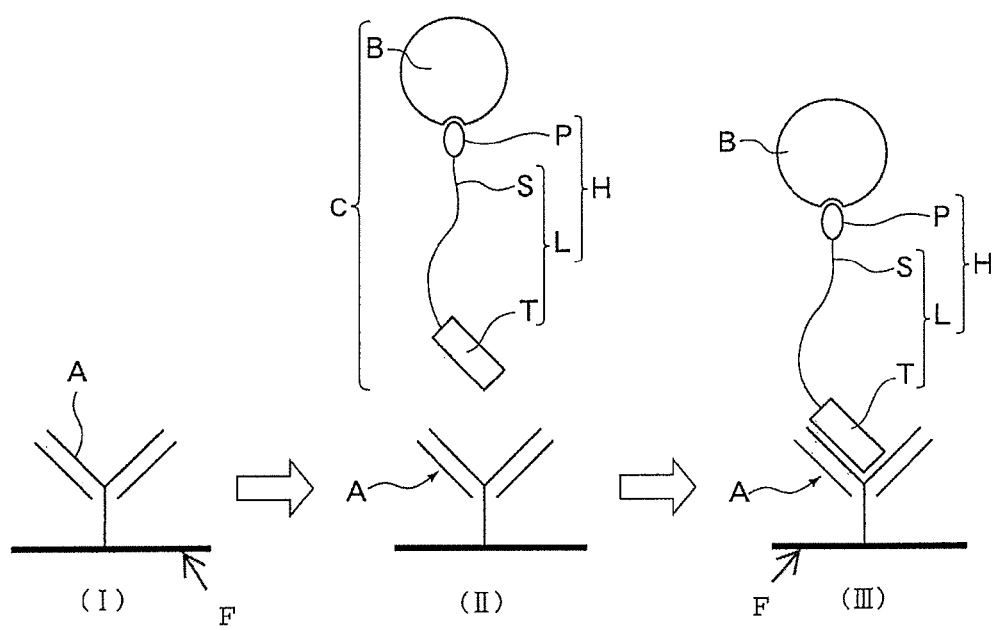

[Fig. 10]
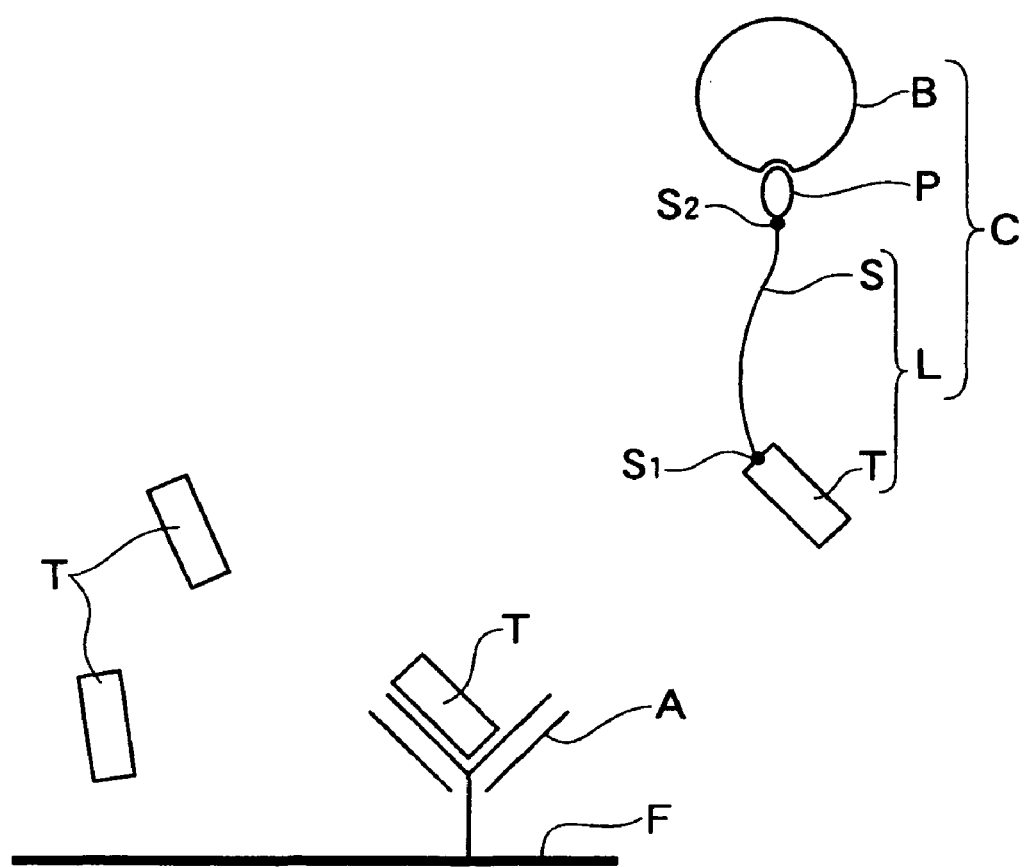

[Fig. 11]
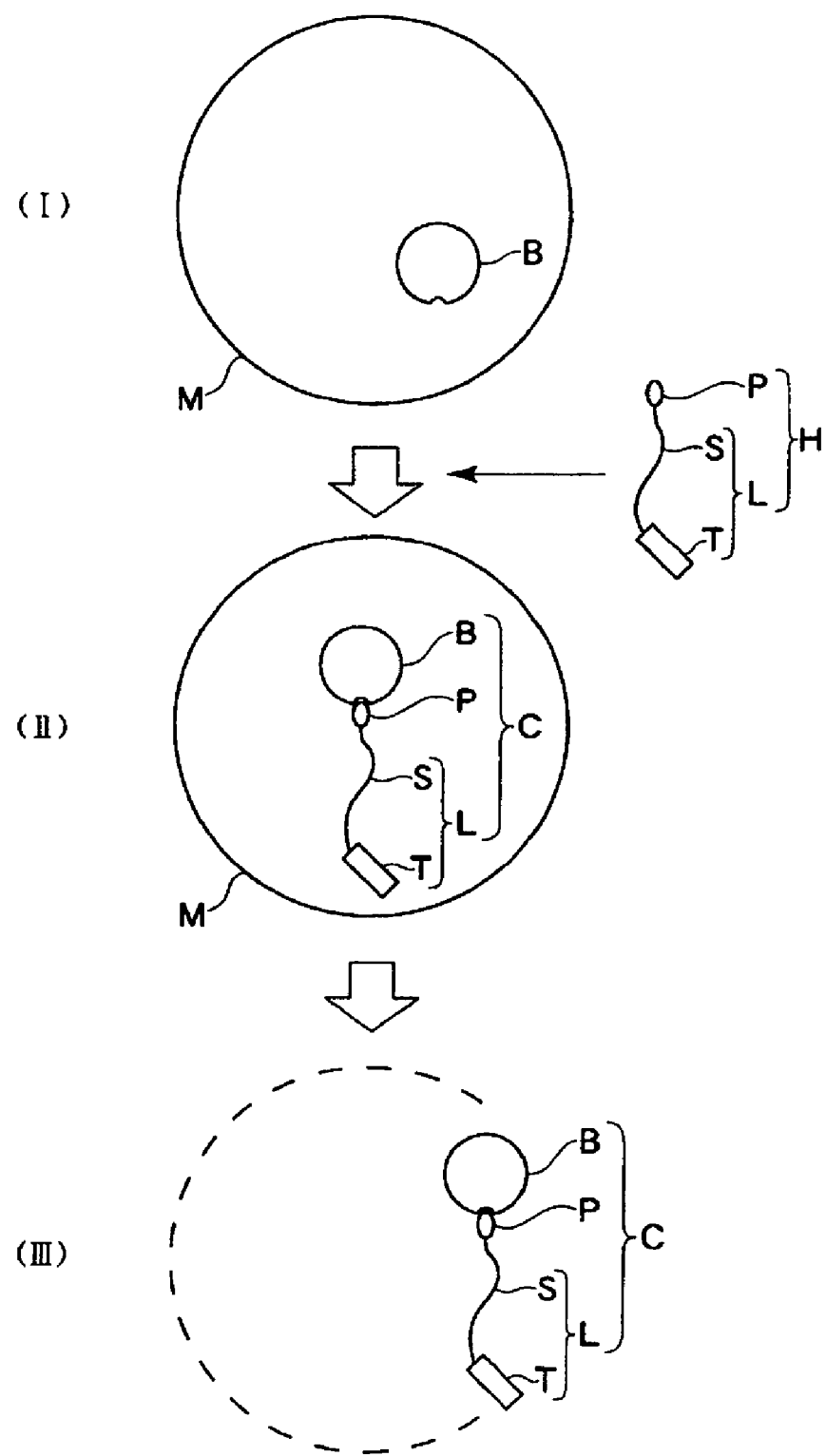

[Fig. 12]
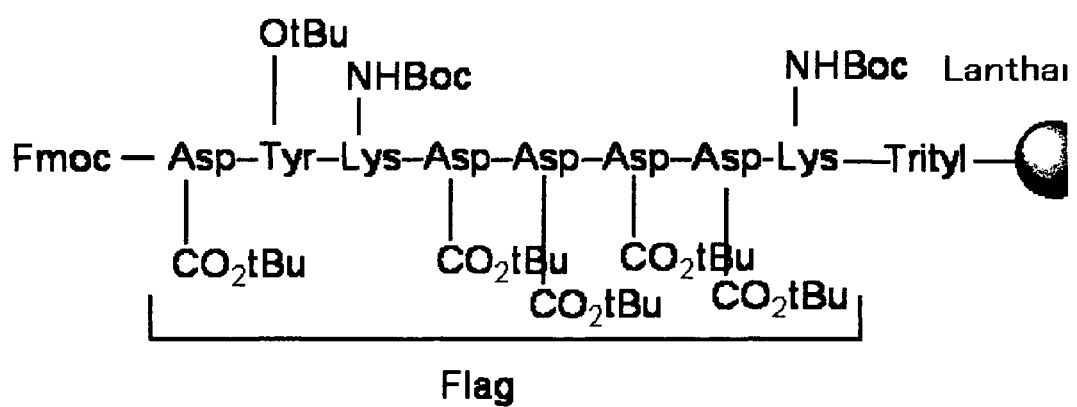

[Fig. 13]
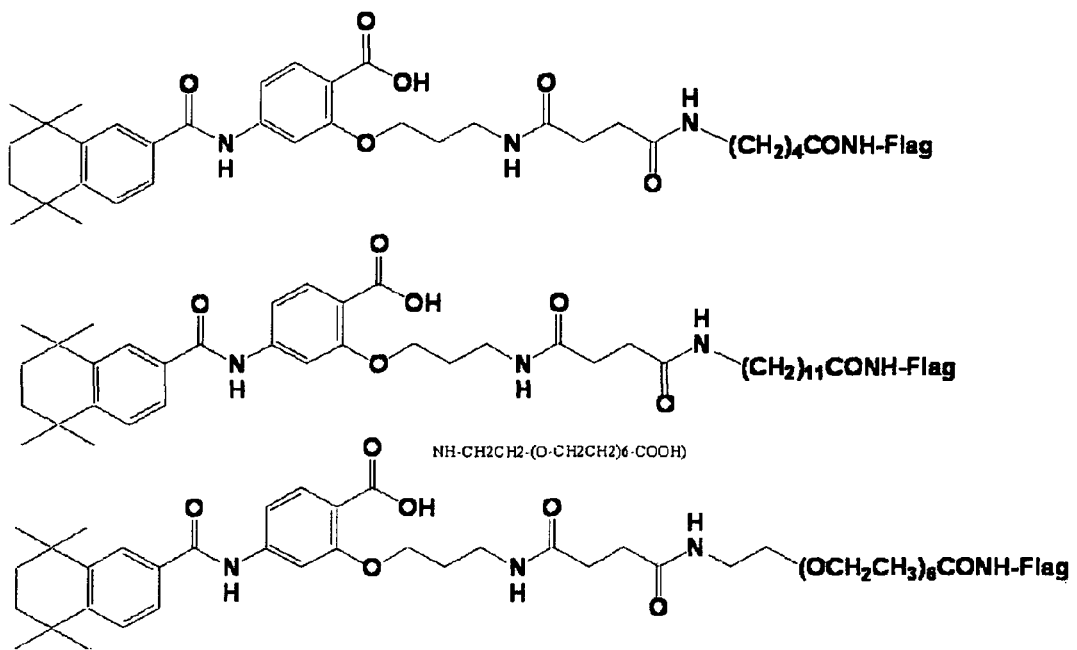

[Fig. 14]
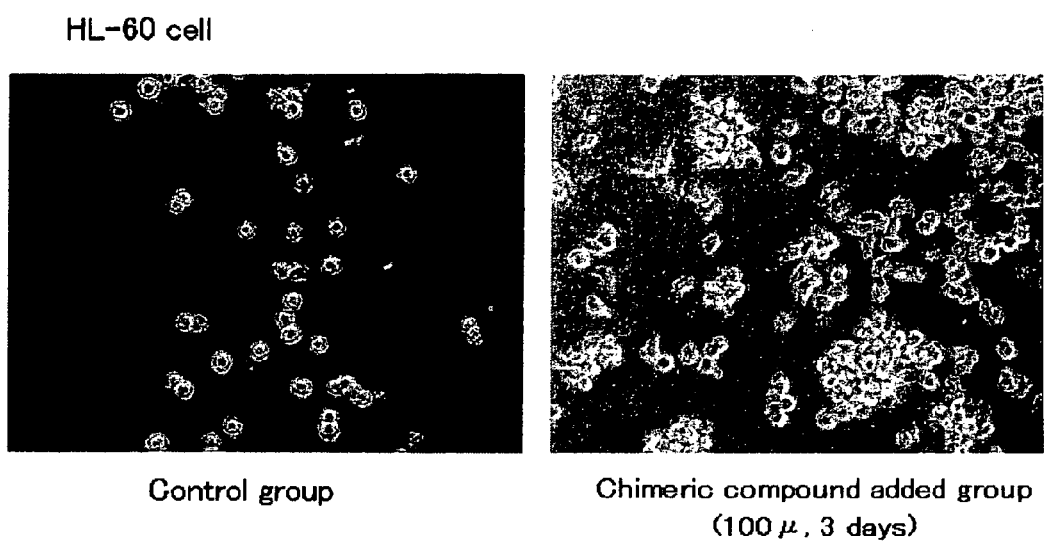
HL-60 cell
Control group
Chimeric compound added group
(100 μ, 3 days)

[Fig. 15]
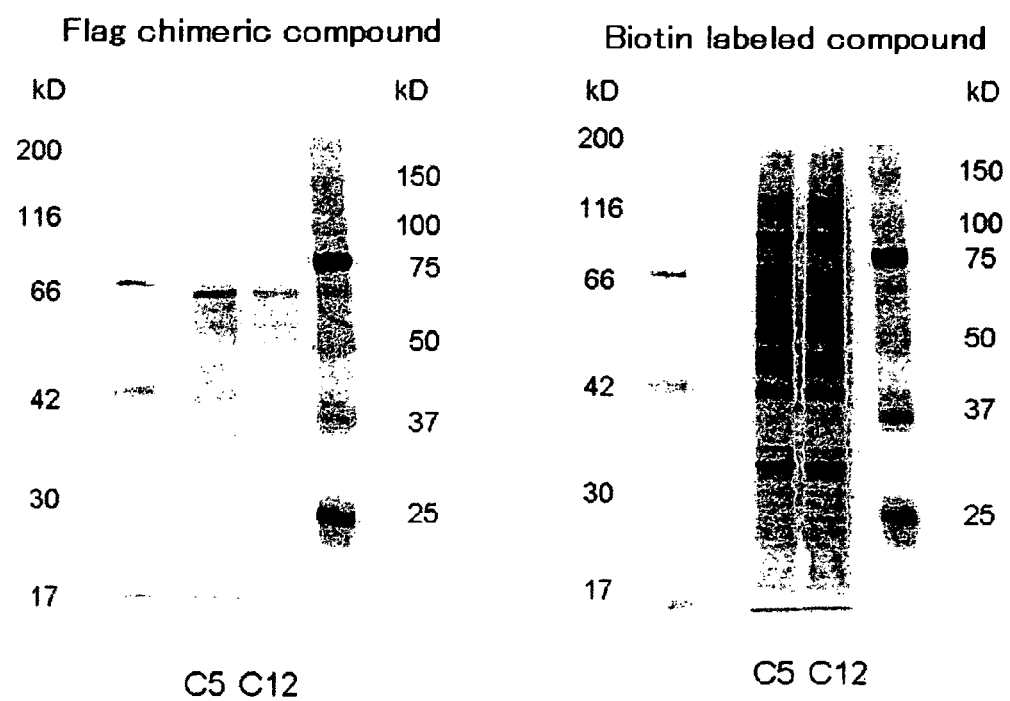

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
```

```
<220> FEATURE:
<223> OTHER INFORMATION: The amino acid sequence of a FLAG peptide

<400> SEQUENCE: 1

Asp Tyr Lys Asp Asp Asp Asp Lys
1               5
```

LABELING SUBSTANCE AND CHIMERIC SUBSTANCE AND METHOD FOR PREPARING THE SAME AND METHOD FOR CAPTURING, STRUCTURALLY ANALYZING AND/OR IDENTIFYING BIOLOGICAL SUBSTANCE BY MEANS OF THE LABELING SUBSTANCE

TECHNICAL FIELD

This invention relates to a labeling substance and a bioassay technology using the labeling substance, wherein the labeling substance is capable of binding a probe substance, which can interact with a biological substance, and has a function to specifically recognize an antibody.

BACKGROUND ART

As a first prior art related to the present invention, a technology can be listed such that after a substance (hereinafter referred to as "probe substance") serving as a probe to detect a target substance is immobilized beforehand to a solid-phase surface such as a metal film, a base plate of a synthetic resin or glass or beads, a specific interaction between substances is utilized to capture and recover the target substance to analyze its structure by mass spectrometry. Use of this technology allows finding a substance interacting with the above-mentioned probe substance.

In the above-mentioned technology, a substance called a linker, spacer or tag can be inserted between the probe substance and a solid-phase surface and labeled to try to adjust a bonding force between the probe substance and the solid-phase surface, resolve steric hindrance and improve the utilization efficiency of the reaction space. Such technology becomes an important elemental technology such as a surface plasmon resonance sensor and a microarray chip with an assembly of DNA and/or protein in a biosensor technology and immunoprecipitation technique.

In general, an "avidin-biotin binding system" is widely used to immobilize the probe substance to the solid-phase surface. Avidin is a glycoprotein to specifically strongly bind to biotin. Because avidin has very high affinity to biotin, it is used to immobilize a biotinylated DNA, peptide and protein.

For example, a solid-phase surface is precoated with avidin such as streptavidin to firmly bind (immobilization) to a biotinylated probe substance. In other cases, the avidin-biotin binding system is widely used in a field of the immunological measurement such as enzyme immunoassay (EIA) and tissue staining.

Some of the prior art using the "avidin-biotin binding system" are listed herein. First, Patent Document 1 discloses a technology, in which after a biotinylated antigen or antibody is bound to avidin or streptavidin immobilized, it is contacted with a solution of a labeling compound to specifically bind to the antibody or antigen in a sample to detect "a labeled antigen-antibody complex." Patent Document 2 also discloses a technology, in which a solution containing a biotinylated probe DNA is spotted onto a solid-phased film, in which an avidin molecule is immobilized as a monolayer, yielding a DNA microarray.

Next, an interactive analysis technology using an "epitope tag peptide" is listed as a second prior technology related to the present invention.

For example, Nonpatent Document 1 discloses a technology below. First, while a recombinant protein fused with an epitope tag peptide is expressed, beads with an immobilized antibody specifically recognizing the epitope tag peptide are mixed with a cell extract. A target protein in the cell extract is trapped via the recombinant protein and then the beads are thoroughly washed, to which an excess amount of the epitope tag peptide is added to replace the protein trapped on the beads with the added peptide to elute the target protein (and a recombinant protein fused) into a liquid phase.

That is, Nonpatent Document 1 discloses an interactive analysis technology using a composition of a "fused protein-peptide tag." This fused protein-peptide tag is one with a series of amino acid sequences between homologous species, so that it can be synthesized using the genetic translation system in an organism.

Patent Document 1: Japanese Published Unexamined Patent Application No. Hei-09-133683
Patent Document 2: Japanese Published Unexamined Patent Application No. 2002-153272
Nonpatent Document 1: Experimental Medicine, Supplementary Volume, Post-Genome Era Experimental Course 2, "Analysis of proteome/frontier technology in protein expression and its functional analysis and study on genomic medicine and drug discovery," Yodosha, Toshiaki Isobe and Nobuhiro Takahashi ed., p. 166-174.

DISCLOSURE OF INVENTION

Problem to be Solved by the Invention

First, when the avidin-biotin binding system is selected for a composition of the solid-phase surface, a strict condition has to be used to dissociate the avidin-biotin binding because of very high affinity of this binding when recovering the biotinylated substance captured by the avidin coated to the solid-phase surface or a complex of this biotinylated substance with another substance. Thereby substances nonspecifically adsorbed on the solid-phase surface could be recovered together to cause a problem interfering with the biotinylated substance which is an analysis target or the target substance showing the interaction with the biotinylated substance during identification.

Moreover, biotin is poor in solubility and difficult to handle so that it has a basic problem with difficulty to be used as a linker. Because biotin itself also readily interacts with unspecified proteins, particularly when a target substance for the identification is protein, use of the biotinylated substance as the probe substance is not preferred. When the biotinylated substance is introduced into a cell, a biopolymer including an unspecified number of proteins is nonspecifically adsorbed on the biotinylated substance so that it is not preferred to use the biotinylated substance as the probe substance.

Furthermore, a conventional interactive analysis technology using a "fused protein-epitope tag peptide" is based on an idea using the fusion of the substances including amino acids together. This technology assumes a technology to synthesize a protein fused with an epitope tag peptide using the translation system in a cell.

An object of the present invention is to provide a labeling substance capable of reversibly immobilizing (reversible detachment) to the solid-phase surface and a technology, in which the labeling substance is used to facilitate recovery of the target substance and the target biological substance interacting with the probe substance bound to the labeling substance can be identified reliably and accurately.

Means for Solving Problems

First, the present invention provides a labeling substance which includes "an organic compound with a chemical structure capable of binding a probe substance, which can interact with the biological substance" and "a peptide bound to the organic compound and specifically recognized by an antibody."

A material composition of the "labeling substance" can be briefly described as one from "organic compound-peptides."

Second, the present invention secondly provides a chimeric substance including "a probe substance except a peptide or protein capable of interacting with the biological substance" and "a peptide directly or indirectly binding to the probe substance and specifically recognized by an antibody." A term "indirectly binding" refers to a binding with another substance intervening between the probe substance and peptide.

A material composition of the "chimeric substance" is briefly described as one composed of either one of (1) a "probe substance (except a peptide or protein)-peptide" and (2) a "probe substance (except a peptide or protein)-mediating substance-peptide."

A "probe substance" includes a substance except a peptide or protein, that is, one not including an amino acid sequence and particularly a low molecular compound which can be brought in view. This allows to provide a complex of a peptide combined with a substance completely different from the peptide and a completely novel "chimeric substance" useful for trapping the target substance.

It can be said that the "chimeric substance" is a complex between heterologous species derived from an idea completely different from a conventional protein fused with an epitope tag peptide because it is not composed of an amino acid alone and cannot be prepared by the genetic translation system in an organism.

As a "probe substance" related to the present invention, in addition to the low molecular compound, a substance except a peptide and protein may be properly used according to its purpose. For example, nucleic acids, lipids, sugars, low molecular weight hormones (except peptide hormones), a toxic substance, an endocrine disrupting substance and a neurotransmitter can be used. If a toxic substance or endocrine disrupting substance is used, a substance interacting with the substance can be identified so that a substance causing its toxicity or mechanism of toxicity can be found.

An "organic compound" which is an essential component of the labeling substance related to the present invention or "organic compound" (mediating substance), which is a possible component of the chimeric substance related to the present invention is a substance to mainly function as a spacer. The organic compound is not narrowly limited to but includes one having a chemical structure capable of binding to the probe substance.

An example of the organic compound includes a lipid or water soluble organic compound with a carboxyl group at least at one terminal and can bind the peptide via the carboxyl group. An organic compound mediates between the probe substance and the peptide allows to select and adjust solventphilic property so that easiness in handling with an assay system and a dynamic state of incorporating into a cell can be freely adjusted.

Next, "peptide" which is an essential component of the labeling substance or chimeric substance related to the present invention is one specifically recognized by an antibody, not limited to but includes an organic compound or a substance capable of binding to the probe substance.

As an example, one allowing to function as an antibody binding tag can be used. For example, an epitope tag peptide such as a Flag peptide (amino acid sequence: Asp-Tyr-Lys-Asp-Asp-Asp-Asp-Lys) (SEQ ID NO: 1) can be used.

In this case, an antibody recognizing this peptide is an anti-epitope tag peptide antibody, for example, anti-Flag peptide antibody.

Third, the present invention provides a "method for labeling the probe substance," in which a probe substance capable of interaction with a biological substance is labeled with a labeling substance including an organic compound and a peptide binding to the organic compound and a peptide specifically recognized by an antibody via one terminal functional group of the organic compound.

Use of this labeling method gives an Example suitable to prepare or manufacture a chimeric substance having a composition of a "probe substance-organic compound-peptide."

Fourth, the present invention provides a "method for preparing a labeling substance," in which a labeling substance or chimeric substance mentioned above can be prepared using a solid-phase method. Use of the "solid-phase method" to prepare or manufacture the labeling substance gives an advantage such as easy control of its synthesis.

For example, after a protective group is introduced into one of the terminal functional groups in the organic compound, the other free terminal functional group is immobilized to the solid support and then the protective group is eliminated from this organic compound to bind to the peptide and then dissociate the organic compound from the solid support to yield the labeling substance composed of the substance of a "organic compound-peptide."

Or, after a protective group is introduced into a predetermined functional group of the peptide and one of the terminal functional group is immobilized to a solid phase, an organic compound is then bound to an N-terminal or C-terminal of this peptide to extend and then the peptide is dissociated from the solid phase to yield a labeling substance having a substance composition of a "organic compound-peptide."

Furthermore, when a probe substance such as a low molecular compound is introduced into a free terminal functional group of an organic compound in the labeling substance and thus prepared, an Example of the chimeric substance having a substance composition of a "probe substance-organic compound-peptide" can be obtained.

Fifth, the present invention provides a "method for capturing a biological substance" using a labeling substance including an organic compound with a chemical structure capable of binding to a probe substance, which can interact with a biological substance and a peptide binding to the organic compound and specifically recognized by an antibody.

Specifically, this provides a "method for capturing a biological substance" performing at least a procedure (A) to guide a sample solution containing a complex of the biological substance including the probe substance to which the labeling substance binds and a biological substance interacting with the probe substance to a region of the solid-phase surface and a procedure (B) to advance the interaction of an antibody immobilized to a solid-phase surface with a peptide in the labeling substance constituting the complex of the biological substance.

In this method, the above-mentioned procedure (A) guides a complex of the biological substance including the substance of a "biological substance-probe substance-labeling substance (organic compound-peptide)" to the solid-phase surface and then forms via procedure (B) a substance composition of a "biological substance-probe substance-labeling substance (organic compound-peptide)-antibody-solid phase." This composition can capture a biological substance on a solid-phase surface via the labeling substance.

Sixth, the present invention provides a "method for analyzing and/or identifying a biological substance" using a labeling substance including an organic compound bound to a probe substance, which interacts with the biological substance and from a peptide bound to the organic compound and specifically recognizing an antibody.

Specifically, this provides a "method for analyzing a biological substance" performing at least a procedure (a) to dissociate a peptide in the label substance from an antibody immobilized to the solid-phase surface, procedure (b) to recover a complex for a biological substance dissociated and procedure (c) to analyze and/or identify the biological substance in the above-mentioned complex of the biological substance.

In this method, a binding between "peptide-antibody" in the substance composed of a "biological substance-probe substance-labeling substance (organic compound-peptide)-antibody-solid phase" is characterized by allowing reversible detachment so that the binding can be dissociated under a mild condition.

This dissociation allows eluting the complex of the biological substance composed of a "biological substance-probe substance-labeling substance (organic compound-peptide)" from the solid-phase surface to be recovered and finally analyze a structure of a target "biological substance" and identify the substance.

Seventh, the present invention provides a "method for recovering an intracellular biological substance."

Specifically, this provides a "method for recovering an intracellular biological substance" performing at least procedures (i) to (iv), in which procedure (i) labeling a probe substance via one terminal functional group of the organic compound with a labeling substance including an organic compound and a peptide bound to the organic compound and specifically recognized by an antibody, procedure (ii) introducing the labeled probe substance into a cell, procedure (iii) advancing in a cell the interaction of the above-mentioned probe substance with the intracellular biological substance and procedure (iv) taking out the complex of the biological substance obtained by the above-mentioned interaction from the cell.

In this method, first, a probe substance is labeled with a substance composed of a "organic compound-peptide" to yield a "probe substance-organic compound-peptide." This substance is then introduced into a cell according to a given procedure to yield in the cell a complex of a biological substance of an "intracellular biological substance-organic compound-peptide," which is taken out from the cell to be recovered. An "intracellular biological substance" includes, for example, proteins, peptides, nucleic acids, sugars, lipids and hormones.

A complex of a biological substance in a sample solution can be captured on a solid-phase surface using a specific binding of an antibody with a peptide in a labeling substance and then dissociated, eluted and recovered in a successive procedure to finally analyze and identify an intracellular biological substance.

A major technical term used in the present invention is herein defined.

A "probe substance" in the present invention refers to a substance functioning as a probe (finder needle) for a target substance, which is a subject in the interaction. A "labeling substance" refers to a substance chemically labeled to the probe substance.

A "chimeric substance" refers to a complex combined with heterologous species such as, for example, "a low molecular compound" with "peptide," "nucleic acid" with "peptide," "sugar" with "peptide" and "lipid" with "peptide," and clearly distinguishes from a cointegrate between homologous species such as a substance composed of a "protein" and "epitope tag peptide."

"Interaction" widely refers to a chemical bond including a noncovalent bond, a covalent bond and a hydrogen bond as well as dissociation between substances and widely includes, for example, hybridization, which is a complementary binding between nucleic acids (nucleotide chain) as well as a specific binding or association with a polymer-polymer, polymer-low molecular and low molecular-low molecule.

A "epitope tag peptide" is an oligopeptide with approximately 10 amino acids, of which a section of an epitope (antigen determinant) in an antibody specifically recognizes. Presently, several kinds of this product including a Flag peptide (Sigma Co.) is commercially available.

EFFECT OF THE INVENTION

A method using a labeling substance or chimeric substance related to the present invention allows dissociating and diluting a complex of a biological substance from a solid-phase surface under a very mild condition because the complex can be reversibly detached from the solid-phase surface. Therefore, a probe substance bound to this labeling substance or a target biological substance trapped by a probe substance constituting a chimeric substance can be easily and freely captured and recovered.

Since the sample for the analysis contains little contamination of substance nonspecifically adsorbed on a solid-phase surface, structural analysis and identification of the target biological substances can be quickly performed with little interference and the results of its identification are very reliable.

Solventphilic property of an organic compound constituting a labeling substance or an organic compound capable of constituting a chimeric substance can be selected or adjusted so that ease in handling in an assay process of the labeling substance or a dynamic stage in incorporation into a cell can be adjusted.

Use of a solid-phase method for preparing or manufacturing a labeling substance and/or chimeric substance allows free control of its synthesis. For example, adjustment of solventphilic property of an organic compound bound to a peptide, selection or adjustment of a structure of the organic compound and designing of a molecular length of a peptide or organic compound can be freely performed according to an object.

BEST MODE FOR CARRYING OUT THE INVENTION

A description is given according to a schematic diagram of FIG. 1, which shows a concept and configuration of the labeling substance and chimeric substance related to the present invention.

Symbols L and H in FIG. 1 respectively indicate a "labeling substance" related to the present invention and an Example of a "chimeric substance" (Example, in which a probe substance complexes with a peptide via an organic compound) related to the present invention. Although not illustrated, a chimeric substance including a probe substance directly bound to a peptide can be used and within a scope of the present invention.

First, a labeling substance L includes an organic compound indicated with a symbol S and a peptide T bound to a terminal site $S_1$ of this organic compound S.

The organic compound S, which is an essential component of the labeling substance L is not limited but can be one with a chemical structure capable of binding to a probe substance P, which can interact with a biological substance.

An organic compound S includes, for example, a lipid or water soluble organic compound with a carboxyl group at least at one terminal $S_1$. In this case, the organic compound S can form an amide bond with the above-mentioned peptide T via the carboxyl group.

Solventphilic property of the organic compound S or adjustment of its level gives an advantage such as allowing to adjust a dynamic stage in incorporation of the labeling substance L into a cell or ease in handling of the assay system.

When this organic compound S functions as a spacer, a linearly extending structure is particularly preferred and its molecular length can be designed according to an object and requirement.

An organic compound S, which is particularly preferable for the labeling substance L related to the present invention is a water soluble organic compound with the following chemical structure (refer to Chemical Equation 1). This organic compound has a polyether chain with a carboxylic group at both terminals.

[Chemical Equation 1]

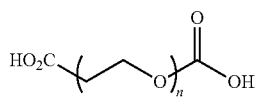

A following candidate for the organic compound S has a polyether chain group similar to the above having an amino group at one terminal (refer to Chemical Equation 2).

[Chemical Equation 2]

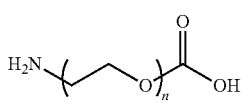

A lipid soluble organic compound with the following chemical structure can be used as the organic compound S (refer to Chemical Equation 3). This organic compound S has an alkyl chain with carboxylic acid at both terminals. Such organic compound S is lipid soluble so that it has high affinity to a biological membrane, and it easily permeates the membrane.

[Chemical Equation 3]

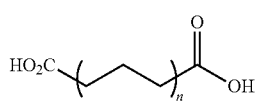

A following candidate for the organic compound S is a lipid soluble organic compound with an alkyl chain with an amino group similar to the above and at one terminal (refer to Chemical Equation 4).

[Chemical Equation 4]

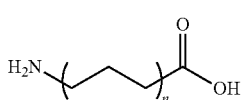

Next, peptide T, which is an essential component of the labeling substance L or chimeric substance H may be used as long as an antibody can specifically recognize it. A binding terminal of the peptide T to an organic compound S or a probe substance P can be either one of a C or N terminal, but is not particularly limited.

The peptide T can function as an antibody binding tag. For example, Flag peptide (amino acid sequence: Asp-Tyr-Lys-Asp-Asp-Asp-Asp-Lys) (SEQ ID NO: 1), which is one kind of an epitope peptide tag can be used according to an object.

FIG. 2 is a schematic diagram to show an antibody immobilized to a solid-phase surface specifically recognizing the peptide T.

A symbol F in FIG. 2 indicates the solid-phase surface. The solid-phase surface F shows a part of a surface of a flat base plate or bead. The solid-phase surface F is, for example, pretreated such that an antibody indicated with A can be immobilized. In the present invention, the solid-phase surface F itself is not narrowly limited to, but includes a surface composition or material, which can firmly immobilize the antibody A.

An antibody A is an antipeptide T antibody, which can specifically recognize peptide T. FIG. 2 shows how the antibody A recognizes the peptide T in the labeling substance L.

More specifically, FIG. 2 shows how biological substance B is captured with the solid-phase surface F, after the probe substance P bound to one terminal of the organic compound S serving as a spacer interacts with a target biological substance B contained in a sample solution R, which is delivered as liquid, added or injected to a region of the solid-phase surface F.

Whether the biological substance B interacts with the probe substance P can be detected by a heretofore known detection principle such as a surface plasmon resonance or crystal oscillator principle.

A representative example of the probe substance P may include a low molecular compound as well as a nucleic acid except a peptide or protein, lipid, sugar, a low molecular hormone (except a peptide hormone), and an endocrine disrupting substance, a toxic substance and a neurotransmitter.

When the probe substance P is a "drug candidate substance," this proves substance P itself could be a drug to target at the disease associated with the biological substance B if a biological substance B as a subject to interact with the probe substance P can be identified.

Next, preferable Examples in the above-mentioned "method for preparing labeling substance L" are described in reference to FIG. 3 to FIG. 5.

Hereinafter, a case that a substance shown in the above-mentioned Chemical Equation 2 is used as a representative example for the organic compound S and Flag peptide is used as peptide T, is described as a representative example, but the present invention is not limited to this.

The labeling substance L can be preferably prepared or manufactured according to a so-called "solid-phase method." A solid support given as symbol X in FIG. 3 includes, for example, Lanterns (Mimotopes Ltd.). Others include a solid support such as polystyrene. When the "solid-phase method" is used to prepare or manufacture the labeling substance, its synthesis is easily controlled.

A linker Y (refer to FIG. 3) used to extend the Flag peptide (symbol T) on the solid support X includes one, in which the Flag peptide T can be cleaved under acidic condition from the solid support X to leave a carboxylic acid group at the terminal of the cleaved peptide.

As a linker Y, for example, a trityl linker can be used. In addition, a chlorotrityl linker, alkoxybenzyl linker or benzyl linker may be used.

An extension reaction of the peptide T uses, for example, the Fmoc method heretofore known. That is, an amino acid (an amino acid side chain is protected with a t-butyl group) protected with a protective group Fmoc is coupled with a solid support X.

Diisopropylcarbodiimide (hereinafter DIC) as a condensing agent is used for this coupling reaction, which runs in the presence of 1-hydroxybenzotriazole (hereinafter HOBt) in DMF at an ambient temperature from several to 48 hours. The product is then washed with DMF and dichloromethane.

After the protective group Fmoc is deprotected with a 20% pyperidine in DMF by standing at an ambient temperature for 30 minutes and then washed, these processes are repeated to advance the extension of the peptide T.

When the peptide T is composed of, for example, only Flag peptide, its amino acid sequence is Asp-Tyr-Lys-Asp-Asp-Asp-Asp-Lys) (SEQ ID NO: 1), whereas when extension of the peptide is desired, an amino acid residue is added.

Addition of the amino acid residue has a limitation, however, it is allowed to use a level of the peptide, which can at least be recognized by antibody A (refer to FIG. 2).

An example shown in FIG. 3 shows a composition, in which single lysine residue (Lys) is inserted at a terminal of the Flag peptide (symbol T). The lysine residue (Lys) added is indicated with an arrow in FIG. 3 for understanding.

Next, a "method for introducing an organic compound S," which functions as a spacer is described. For example, as shown in FIG. 4, a polyether chain (for example, n=5) with a carboxylic acid group at least at one terminal is introduced to a terminal amino group of the Flag peptide used as a peptide T.

This introduction method may use DIC as a condensing agent as shown in FIG. 4. As an organic compound S, in addition to the water soluble substance (one given in Chemical Equation 2), a similar water soluble substance in a Chemical Equation 1 or a lipid soluble substance (including one with an alkyl chain) in the above-mentioned Chemical Equations 3 and 4 may be used.

Introduction of an alkyl chain into the amino group of the terminal lysine residue in the Flag peptide appears to be effective in order to have amphipathicity in the labeling substance L obtained. For example, the labeling substance L with the chemical structure given in FIG. 5 is preferable to show amphiphacity.

Three preferable Examples related to a "method for labeling a labeling substance L," that is, a "method for preparing a chimeric substance H of one Example (example to mediate with an organic compound S, refer to FIG. 1) for a probe substance P are described in order with reference to FIG. 6 to FIG. 8. In the following Example, a case that the probe substance P is a low molecular compound is taken as a representative example for description.

A first example shown in FIG. 6 uses a retinoid receptor agonist applied to a cancer drug as the probe substance P. FIG. 6 shows a reaction, in which the retinoid receptor agonist indicated with a symbol $P_1$ forms an amide bond with a terminal amino group of the labeling substance L.

The terminal carboxyl group of the compound $P_1$ is reacted with the terminal amino group of the labeling substance L in the presence of DIC and HOBt in N,N-dimethylformamide (DMF) or a 9:1 mixture of DMF-dichloromethane at an ambient temperature for 24 to 48 hours to form the amide bond.

Cleavage from the solid support X (when a trityl linker is used) and deprotection of the lysine residue in the Flag peptide section are then carried out with 1% TFA/dichloromethane. Deprotection of all amino acids in the Flag peptide section is performed with a 9:1 mixture of TFA:$H_2O$.

Next, two other Examples of the probe substance P will be given. FIG. 7 shows a first example. In this example, an organic compound S, as a spacer, which has a free terminal carboxyl group is used and coupled via N-hydroxysuccinimide with an amino group of a low molecular weight drug candidate substance with a chemical structure indicated with a symbol $P_2$ in FIG. 7 (formation of amide bond). This reaction can be carried out in the presence of N-hydroxysuccinimide and DIC in DMF at an ambient temperature for 24 to 48 hours.

An example given in FIG. 8 uses a coupling method, in which a low molecular weight drug candidate substance $P_3$, of which the terminal amino group is bromoacetylated is reacted with a labeling substance (symbol Lc) having one cysteinyl terminal in the organic compound S as a spacer in the presence of triethylamine in DMF at an ambient temperature for 24 to 48 hours.

The above-mentioned bromoacetylation easily advances by treating with bromoacetyl chloride in a mixture of dichloromethane and pyridine.

When a hydroxyl group in the compound is used, the hydroxyl group is bonded with an active form of adipic acid ($HO_2C(CH_2)_4CO_2H$) or pimelic acid ($HO_2C(CH_2)_5CO_2H$) using an intervening compound reactive with an amino group. In all of these reactions, DIC can be used to form ester and amide bonds.

A method for capturing, recovering, structurally analyzing and identifying a biological substance B present inside and outside a cell using a chimeric substance H including the probe substance P and labeling substance L according to the above-mentioned manner is described below. FIG. 9 and FIG. 10 are a flowchart to briefly show a process associated with the method.

<Method for Capturing Biological Substance>

FIG. 9 briefly shows a process flowchart of a "method for capturing a biological substance" related to the present invention. An antibody A specifically recognizing a peptide T in a labeling substance L (chimeric substance H) is immobilized to a given solid-phase surface F beforehand (refer to FIG. 9 (I)).

Next, a sample solution R containing a complex of the biological substance C, which includes a complex including the labeling substance L and probe substance P (that is, chimeric substance H) and a biological substance B interacting with the probe substance P in the chimeric substance H (for example, protein) is delivered to a region of the above-mentioned solid-phase surface F (refer to FIG. 9 (II)).

The antibody A immobilized to the solid-phase surface F is advanced to be interacted with the peptide T constituting the complex of the biological substance C (refer to FIG. 9 (III)). By executing this procedure, the biological substance B can be captured on the solid-phase surface F via the probe substance P and labeling substance L.

An antibody A immobilized to the solid-phase surface F is next dissociated from the peptide T in the complex of the biological substance C (refer to FIG. 10).

In this dissociation method, an excess amount of the peptide T itself is added to a region of the solid-phase surface F to replace the peptide T in the labeling substance L recognized and trapped by the antibody A and eluted as complex C accompanied by the biological substance B into a liquid phase (refer to FIG. 10)).

FIG. 10 attached schematically shows how excessively-added free peptide T can replace the peptide T to elute and free the complex C including the biological substance B, the probe substance P and the labeling substance L.

Next, the dissociated complex of the biological substance C is recovered from the solid-phase surface F and the biological substance B in the complex of the biological substance C is structurally analyzed. Furthermore, the biological substance to show specific interaction with the probe substance P is identified.

<Method for Recovering Biological Substance Present in a Cell (Intracellular Biological Substance)>

First, a selected probe substance P is labeled with a labeling substance L including an organic compound S and a peptide T bound to the organic compound S and capable of specifically recognizing an antibody A via a terminal functional group in the organic compound S (refer to a "method for labeling to labeling substance L" already described) to prepare a chimeric substance H including an intervening organic compound S.

Next, the chimeric substance H obtained by labeling is introduced into a cell. Specifically, the chimeric substance H is dissolved with an appropriate buffer (150 mM NaCl, Tris 50 mM, pH 7.4 or the like).

FIG. 11 is a schematic diagram to show how the chimeric substance H is introduced into a cell indicated with a symbol M. FIG. 11 (I) shows how the target biological substance B exists in the cell M.

When the chimeric substance is difficult to directly dissolve, it is once dissolved in dimethyl sulfoxide (DMSO) and then diluted with the above-mentioned buffer or the like, which is added to a culture fluid containing a culture cell such as a HEK293 cell (human embryonic kindney culture cell).

When the chimeric substance H is not incorporated into the cell M in direct addition to the culture medium, Polyfect Transfection Reagent (Qiagen Ltd.) is used to transfect the chimeric substance H into the cell M to culture for an appropriate period of time (24 to 48 hours).

This can advance the interaction in the cell M between the probe substance P in the chimeric substance H and the biological substance B in the cell M. For example, the probe substance P binds to a particular protein (biological substance B) in the cell M to form a complex of the biological substance C (refer to FIG. 11 (II)).

Next, an operation is executed such that the complex of biological substance C obtained by the above-mentioned interaction is taken out from the cell M.

For example, using the amino acid sequence of the peptide T contained in the labeling substance L bound to the probe substance P, "immunoprecipitation" heretofore known, which uses an antibody A against the amino acid sequence is used to extract the complex of the biological substance C from the cell M (refer to FIG. 11 (III)).

An example of an extraction method is given below. A probe substance P labeled with the labeling substance L, that is, a cell M introduced with a substance corresponding to the chimeric substance H is solubilized with a solubilizing buffer (for example, 20 mM HEPES, pH 7.5, 150 mM NaCl, 50 mM NaF, 1 mM $Na_3VO_4$, 1 mM PMSF, 1% Triton X100). After addition of the buffer, the cell M is scraped to recover in a centrifuging tube and subject to ultracentrifuge (55,000 rpm, 4° C., 20 minutes).

Then, the antibody A immobilized beforehand to the solid-phase surface F is advanced to be interacted with the peptide T in the labeling substance L constituting the complex of the biological substance C (refer again to FIG. 2).

For example, agarose beads (Sigma Co.), to which the antibody A specifically recognizing a particular amino acid sequence is immobilized is added to the cell extract (supernatant) after centrifugation and stirred at 4° C. for 3 hours to advance the above-mentioned interaction.

Next, the intracellular biological substance B in the above-mentioned complex of the biological substance C is structurally analyzed and then identified.

For example, after the above-mentioned beads after washing are centrifuged (1,000 rpm, 4° C. 1 minute) to be collected and washed with the solubilizing buffer, a buffer containing a Flag peptide (symbol T) is added to elute the probe P bound to the beads (refer to FIG. 10) and recover the complex C including the target intracellular biological substance B interacting with the probe substance P and the labeling substance L, and the structure of the biological substance B among them is analyzed and the biological substance B can be identified.

When an Example, in which the target intracellular biological substance B is a protein is described, the target protein to be a subject for the interaction after recovery of the complex C can be identified by a heretofore known method called "mass tag method" using a heretofore known tandem mass spectrometer (MS/MS) (Toshiaki Isobe and Nobuhiro Takahashi ed., "Analytical method of proteome," Yohdosha, p. 129-p. 142). A practical procedure is as follows.

First, after a recovered sample is centrifuged to concentrate, it is dissolved in a buffer for an enzymatic reaction (100 mM Tris, pH 8.8). Then, the sample is then digested and decomposed with an enzyme "trypsin" or "lysyl-end peptidase" which recognizes and cleaves a particular amino acid. Thereby, lysyl-end peptidase is added to the mixture in a ratio of the enzyme to substrate (by weight) of 1/100 to 1/50 to react at 37° C. for 12 hours to yield a digested product. The digested product is measured by the tandem mass spectrometer to obtain a mass value of each peptide decomposed and information of the internal amino acid sequence.

Using the mass value of the peptide fragment digested by the enzyme, a database is automatically retrieved to select a sequence of the candidate amino acid, which is used to calculate a set of the mass value for each amino acid fragmented from its sequence.

The above-mentioned database, which has been publicly released is used from "SwissProt" (web address: ftp.ebi.ac.uk/pub/database/sp_tr_nrdb/fasta/sprot.fas.Z) as the protein database and "NCBI RefSeq" (web address: ncbi.nih.gov/refseq/H_sapiens/mRNA_Prot/hs.faa.gz) as the nucleic acid database, respectively.

Example 1

Example for Synthesis of Chimeric Compound

Lanterns (Mimotopes Co.) substituted with a trityl group were used as a solid support. Ten pieces of Lanterns were placed in an appropriate size of a vial, to which 10 ml of a mixture of acetyl chloride and dichloromethane (1:1) was added and kept for 12 hours. After the reaction, the reaction product was washed with dimethylformamide (hereinafter "DMF") for 5 minutes three times and then with dichloromethane three times for 5 minutes.

469 mg (0.1 M) of Fmoc-Lys(N-Boc)-OH (Calbiochem Ltd.) was then dissolved in 10 ml of dichloromethane (hereinafter "DCM") and reacted with the pretreated solid support in the presence of 0.44 ml (0.25 M) of N,N-diisopropylethylamine (hereinafter "DIEA") for 12 hours. After the reaction, the reaction product was washed with the above-mentioned DMF for 5 minutes three times and then with dichloromethane for 5 minutes three times.

The reaction product was treated with 10 ml of 20% piperidine (as DMF solution) for 30 minutes in order to release the Fmoc protective group of the amino acid residue. After the reaction, the reaction product was washed with DMF for 5 minutes three times and then with dichloromethane for 5 minutes three times. 411 mg (0.1 M) of Fmoc-Asp(O-t-Bu)-OH (Calbiochem Ltd.) was dissolved in 10 ml of DMF and reacted with the Lanterns for 12 hours for condensation in the presence of 0.19 ml (0.12 M) of diisopropylcarbodiimde (hereinafter "DIC") and 162 mg (0.12 M) of 1-hydroxybenzotriazole (hereinafter "HOBt"). A similar method was repeated three times using the Fmoc-Asp(O-t-Bu)-OH residue to complete the condensation.

469 mg (0.1 M) of Fmoc-Lys(N-Boc)-OH (Calbiochem Ltd.) was dissolved in 10 ml of DMF and reacted with the Lanterns for 12 hours in the presence of 0.19 M (0.12 M) of DIC and 162 mg (0.12 M) of HOBt for condensation. After Fmoc was released similarly to the above and washed, 460 mg (0.1 M) of Fmoc-Tyr(O-t-Bu)-OH (Calbiochem Ltd.) was dissolved in 10 ml of DMF and reacted with the Lanterns for 12 hours in the presence of 0.19 ml (0.12 M) of DIC and 162 mg (0.12 M) of HOBt for condensation.

An Asp (asparagine acid), which is a final residue of the Flag peptide was similarly condensed to the Lantern according to the above-mentioned method for preparing a Flag peptide, which was substituted with each protective group. A composition of the obtained Flag peptide is shown in FIG. 12.

The Flag peptide was then condensed with a C5 alkyl group (Fmoc-NH—$(CH_2)_4$—COOH), a C12 alkyl chain of carboxylic acid (Fmoc-NH—$(CH_2)_{11}$—COOH) or a polyether chain of carboxylic acid (Fmoc-NH—$CH_2CH_2$—(O—$CH_2CH_2)_6$—COOH) including six condensed diethyl ether groups.

In condensation with the C5 alkyl group of carboxylic acid, one vial of the Flag Lantern mentioned above was reacted with 4 mg of Fmoc-NH—$(CH_2)_4$—COOH for 12 hours in the presence of 52 mg (0.1 M) of PyBoc in 1 ml of a DMF/DCM (9:1) solution as a condensing agent and 34.8 ml of DIEA. Using a similar reaction condition, Flag peptides condensed with the C12 alkyl chain of carboxylic acid or polyether chain were prepared using 43.8 mg of (Fmoc-NH—$(CH_2)_{11}$—COOH and 57.6 mg of Fmoc-NH—$CH_2CH_2$—(O—$CH_2CH_2)_6$—COOH, respectively.

Flag peptides condensed with various spacers were condensed with various drugs to prepare a chimeric compound. As an example, "retinoid receptor agonist" given in following Chemical Equation 5 termed with JS-603A-1 was condensed to prepare a chimeric compound.

[Chemical Equation 5]

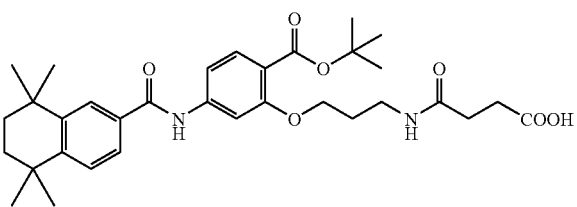

11.2 mg of JS-603A-1 was dissolved in 190 ml of DMF and condensed with a roll of Flag spacer Lantern prepared as mentioned above in the presence of 3 mg of HOBt and 3.6 µL of DIC. 1% TFA (DCM solution) was used to dissociate the chimeric compound from the solid support and then 90% aqueous TFA solution was used to release each protective group to prepare the chimeric compound with a structure given in FIG. 13.

Example 2

Example to Demonstrate Effectiveness of Chimeric Compound (1) First, it was investigated if the chimeric compound related to the present invention maintains the function of conventional retinoid receptor agonist.

Biological activity was studied using a differential promotion activity in a hemocyte related cancer cell, an HL-60 cell as an indicator. A cell was cultured in a RPMI1640 medium (10% FBS+antibiotic) and a drug was diluted with the medium to adjust the final concentration to 1% and cultured in an incubator under carbon dioxide for 3 to 10 days.

As a result, as shown in an alternative picture for drawing in FIG. 14, it was observed in a group treated with the chimeric compound (100 µM, 3 days) with a C5 alkyl chain as a spacer that a cell was differentiated from a spherical floating cell to a flat adherent cell (refer to the picture at the right in FIG. 14). This finding reveals that the chimeric compound maintains the activity of the original retinoid receptor agonist. This result proves the chimeric compound related to the present invention is one simultaneously having the biological activity as a Flag peptide and a drug.

(2) Next, it was investigated if the chimeric compound related to the present invention could be used to identify a target protein.

A concentration of an HEK293 cell was adjusted to $1.0 \times 10^5$ cells/ml and 10 ml of this solution was inoculated on a 10 cm petri dish to culture overnight. A cultured cell was dissolved in a cell dissolving buffer, recovered and centrifuged to yield a supernatant. Six to twelve nmoles of the chimeric compound labeled with the Flag peptide was added to the supernatant obtained and gently stirred for 1 hour. This supernatant was then mixed with an antiFlag antibody binding agarose gel and gently stirred for 1 hour.

After centrifugation, the supernatant was suctioned to eliminate and the gel was washed with a washing buffer and an elution buffer. After being centrifuged and the washing was suctioned to eliminate, a 0.5 mg/ml of Flag peptide solution was used to elute a complex of the Flag labeled compound with a protein from the gel. The eluant was transferred to a different Eppendorf tube, to which 1% deoxycholic acid and trichloroacetic acid were added, centrifuged and washed with acetone to yield a trichloroacetate salt as a pellet. The obtained pellet was dissolved with a 1×SDS sample buffer. After the obtained sample was electrophoresed with a 10% acrylamide gel (SDS-PAGE), a silver staining kit was used to visualize the protein band to sliver-stain the obtained protein.

The chimeric compound used in this experiment is a compound with C5 and C12 alkyl chains as a spacer. The results for identification of the target protein are shown in FIG. 15 (an alternative picture for drawing).

As found in the results in FIG. 15, when a Flag chimeric compound is used, a clear band which appears to be a retinoid receptor can be confirmed near 60 kDa, whereas when a conventional biotin labeled compound (Comparative Example) is used, many bands which could be derived from nonspecific adsorption are irregularly contained so that bands cannot be identified (refer to the picture at the right in FIG. 15).

The band at 60 kDa bound to the chimeric compound was spliced from the gel and identified to be a retinoid receptor using a heretofore known method called "mass tag method," which uses a heretofore known tandem mass spectrometer (MS/MS). (Toshiaki Isobe and Nobuhiro Takahashi ed., "Analytical method of proteome," Yohdosha Publisher, p 129-p 142). A practical procedure is given below.

A buffer for an enzymatic reaction (100 mM Tirs, pH 8.8) was added to the spliced gel. The spliced product was then digested and decomposed with an enzyme "trypsin" or "lysyl-end peptidase," which recognizes and cleaves a particular amino acid. In this experiment a lysil-end peptadase was used. Lysyl-end peptidase was added in a ratio of the enzyme to substrate (by weight) of 1/100 to 1/50 to react at 37° C. for 12 hours to yield a digested product. The digested product was analyzed by the tandem mass spectrometer to obtain a mass value of each decomposed peptide and information on the internal amino acid sequence. Using the mass value of the peptide fragment digested by the enzyme, a database was automatically retrieved to select a sequence of the candidate amino acid, which was used to calculate a set of the mass value for each amino acid fragmented from its sequence.

The above-mentioned database which has been publicly released is used from "SwissProt" (web address: ftp.ebi-.ac.uk/pub/database/sp_tr_nrdb/fasta/sprot.fas.Z) as the protein database and "NCBI RefSeq" (web address: ftp.ncbi.nih.gov/refseq/H_sapiens/mRNA_Prot/hs.faa.gz) as a nucleic acid database, respectively.

INDUSTRIAL APPLICABILITY

The present invention allows reliably capturing and recovering a substance, which interacts with a probe substance so that it can be applied to accurate identification of a target biological substance. For example, a substance interacting with a drug candidate compound can be reliably identified. When a toxic substance or endocrine disrupting substance is targeted, a substance interacting with the target substance can be identified so that a substance to cause toxicity, etc., and its mechanism can be found.

BRIEF DESCRIPTION OF THE DRAWINGS

FIG. 1 is a schematic diagram to show the principle and components in one example using a labeling substance (L) and a chimeric substance (H) related to the present invention;

FIG. 2 is a schematic diagram to show how an antibody (A) immobilized to a solid-phase surface (F) specifically recognizes a peptide (T) in a labeling substance (L);

FIG. 3 is a diagram to show a composition, in which single lysine residue (Lys) is inserted at a terminal of a Flag peptide bound to a solid support (X) via a linker (Y);

FIG. 4 is a diagram to show one example, in which an organic compound (S) is introduced to a FLAG peptide (T) bound to a solid support (X);

FIG. 5 is a diagram to show one example of a chemical structure of an amphipathic labeling substance (L);

FIG. 6 is a diagram to show a suitable example for a method for labeling to a probe substance (P) with a labeling substance (L) (a method for preparing a chimeric substance H);

FIG. 7 is a diagram to show another Example suitable for the same method;

FIG. 8 is a diagram to show further another Example suitable for the same method;

FIG. 9 is a diagram to briefly show a process flow in a "method for capturing a biological substance" related to the present invention;

FIG. 10 is a diagram to schematically show how a complex of a biological substance (C) is substituted with excessively-added peptide to elute and release in a liquid phase;

FIG. 11 is a diagram to show how a complex of a labeling substance (L) with a probe substance (P) is introduced into or taken out from a cell (M);

FIG. 12 is a diagram to show a composition (structure) of a Flag peptide obtained in the experiment related to Example 1;

FIG. 13 is a diagram to show a composition (structure) of a chimeric compound obtained in the experiment related to Example 1;

FIG. 14 is an alternative picture for drawing to show the experimental results related to Example 2 (an alternative picture for drawing, which shows a cell in a group treated with a chimeric compound with a C5 alkyl chain as a spacer is differentiated from a spherical floating cell to a flat adhering cell). The picture at the right is one related to the Example and the picture at the left is one related to a control group; and FIG. 15 is an another alternative picture for drawing to show the experimental results related to Example 2 (an alternative picture for drawing to show the results for identification of a target protein). The picture at the left is one related to the Example and the picture at the right is one related to the Comparative Example.

DESCRIPTION OF SYMBOLS

| A: | Antibody |
|---|---|
| B: | Biological substance/intracellular biological substance |
| F: | Solid-phase surface |
| H: | Chimeric substance (complex of heterologous species of peptide and probe substance) |
| L, Lc | labeling substance |
| M: | Cell |
| P ($P_1$, $P_2$ and $P_3$): | probe substance |
| S: | Organic compound |
| T: | Peptide (for example, epitope tag peptide) |
| X: | Solid support |

What is claimed is:

1. A method for capturing a biological substance comprising at least the following:
   (A) guiding a sample solution containing a complex of the biological substance and a chimeric substance to a region of a solid surface, the chimeric substance comprising a probe substance, except a peptide or protein, capable of interacting with the biological substance, an epitope tag peptide recognized by an antibody, which antibody is immobilized to a solid surface, and an organic compound having a chemical structure capable of Covalently binding to both the probe substance and the epitope tag peptide;
   (B) enabling the interaction of said antibody immobilized to the solid surface with the epitope tag peptide in the chimeric substance included in the complex.

2. A method for capturing the biological substance described in claim 1 wherein the biological substance is any one of protein, peptide, nucleic acid, sugar, lipid or hormone.

3. A method according to claim 1, wherein the chimeric substance allows for reversible detachment to the solid surface.

4. A method described in claim 1, wherein the chimeric substance capable of interacting with the biological substance provides a binding which allows reversible detachment.

5. A method described in claim 4, where the binding can be disassociated under mild conditions.

6. A method described in claim 1, wherein the organic compound is a compound of formula

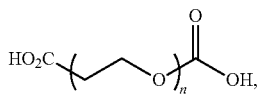

a compound of formula

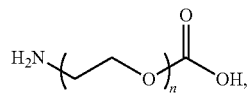

a compound of formula

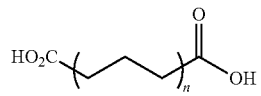

or a compound of formula

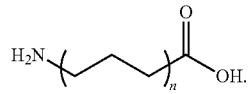

7. The method of claim 1, wherein the probe substance is a retinoid receptor agonist.

8. The method of claim 1, wherein the epitope tag peptide is a Flag peptide, having amino acid sequence: Asp-Tyr-Lys-Asp-Asp-Asp-Asp-Lys (SEQ ID No. 1).

* * * * *